United States Patent
Scholan

(10) Patent No.: US 10,420,617 B2
(45) Date of Patent: Sep. 24, 2019

(54) CHARACTERISING MOTION CONSTRAINTS

(71) Applicant: CMR SURGICAL LIMITED, Cambridge, Cambridgeshire (GB)

(72) Inventor: Andrew Scholan, Suffolk (GB)

(73) Assignee: CMR SURICAL LIMITED, Cambridge, Cambridgeshire (GB)

(*) Notice: Subject to any disclaimer, the term of this patent is extended or adjusted under 35 U.S.C. 154(b) by 316 days.

(21) Appl. No.: 15/524,182

(22) PCT Filed: Oct. 30, 2015

(86) PCT No.: PCT/GB2015/053280
§ 371 (c)(1),
(2) Date: May 3, 2017

(87) PCT Pub. No.: WO2016/071674
PCT Pub. Date: May 12, 2016

(65) Prior Publication Data
US 2017/0367774 A1    Dec. 28, 2017

(30) Foreign Application Priority Data

Nov. 4, 2014 (GB) .................................. 1419645.5
Mar. 20, 2015 (GB) .................................. 1504786.3

(51) Int. Cl.
*G06F 19/00* (2018.01)
*A61B 34/30* (2016.01)
(Continued)

(52) U.S. Cl.
CPC .............. *A61B 34/30* (2016.02); *B25J 3/04* (2013.01); *B25J 9/1689* (2013.01); *A61B 2017/00725* (2013.01)

(58) Field of Classification Search
CPC combination set(s) only.
See application file for complete search history.

(56) References Cited

U.S. PATENT DOCUMENTS

2013/0116706 A1    5/2013 Lee et al.
2014/0195052 A1    7/2014 Tsusaka et al.

FOREIGN PATENT DOCUMENTS

WO    WO 00/51486    9/2000
WO    WO 2006/124390    11/2006

OTHER PUBLICATIONS

Search Report from International PCT/GB2015/053280.
GB Search Report for GB1419645.5.
GB Search Report for GB 1504786.3.

*Primary Examiner* — Bhavesh V Amin
(74) *Attorney, Agent, or Firm* — Husch Blackwell LLP

(57) ABSTRACT

A robot comprising: a base; a flexible arm extending from the base and having a plurality of joints whereby the configuration of the arm can be altered, a plurality of drivers arranged to drive the joints to move, a plurality of sensors for sensing the position of each of the joints and an attachment structure for attaching a tool to the arm, the joints permitting the angular attitude of the attachment structure relative to the base to be varied; and a control unit configured to control the drivers and to receive inputs from the sensors, and operable in a calibration mode in which, while a tool is attached to the attachment structure and captive in a port, it: (i) controls the drivers so as to permit the arm to be reconfigured by the action of an external force applied to the arm; (ii) monitors the configuration of the arm under the presence of an external force applied to the arm and transmitted through the tool to the port so as to cause the attitude of the attachment structure to the base to alter; whereby the location of the port can be estimated.

14 Claims, 2 Drawing Sheets

(51) Int. Cl.
  *B25J 3/04*    (2006.01)
  *B25J 9/16*    (2006.01)
  *A61B 17/00*    (2006.01)

CHARACTERISING MOTION CONSTRAINTS

This invention relates to characterising mechanical constraints on the motion of a machine such as a robot, particularly a surgical robot.

FIG. 1 illustrates a surgical robot 1 in the course of performing an invasive medical procedure on a patient 9. The robot comprises an arm 2 which is articulated by means of multiple flexible joints 3 along its length. At the distal end 4 of the arm is a surgical tool. The surgical tool has a thin elongate shaft 5 with a device 6 at its distal end for engaging in the medical procedure. The device could, for example, be a cutting, grasping or imaging device. The surgical tool is attached to the arm via a wrist joint 3a of the arm. The wrist joint is configurable to adjust the direction in which the shaft 5 extends whilst the majority of the arm 2 remains static. The surgical tool is inserted into the patient's body through a surgical port 7. The port has a hollow tube 8 which passes through the outer tissues of the patient to help limit disruption to those tissues as tools are inserted and removed, and as the robot manipulates the tools within the patient's body.

To reduce disruption to the patient's outer tissues it is preferable for the robot to manipulate the tool so that the tool does not stress those tissues by imposing a significant lateral force on the port. One way to achieve this is for an operator of the robot to manually control the configuration of wrist 7 of the robot so that wherever the wrist is positioned, the tool is directed from the wrist so as to pass through the centre of the port. However, to manually control the attitude of the tool in this way in coordination with movement of the wrist imposes a high workload on the operator and requires a high degree of skill. It is preferable for the control systems of the robot to intervene automatically to help the operator to keep the tool positioned through the natural location of the port. In order to achieve that function, the control systems must know the location of the port relative to the robot. Since the location of the port varies from patient to patient, that requires the control systems to learn the port's location at the start of each procedure.

One way to learn the port's location is for a technician to measure the offset and direction of the port from a datum point on the robot at the start of the procedure, and to provide that information to the robot's control systems. That approach is inconvenient and risks errors in the data entry process. Another approach might be for the technician to attach a measurement tool of known length to the robot, and to manually control the robot until the tip of the tool is touching the port. If the robot is equipped with sensors that can sense the state of each of its joints then that information, together with the distances between the joints and the length of the measurement tool might automatically be combined geometrically so as to determine the position of the port relative to a datum point on the robot. This process would have the advantage of permitting the measurements to be taken automatically. However, it would require a somewhat artificial operation by the technician.

Furthermore, each of these approaches involves measuring the position of the outer part of the port. In practice, the tube of the port will extend for some distance, e.g. 50 to 100 mm, through the outer tissues of the patient. To reduce the overall lateral stress on those tissues it would be preferable for the robot to assist the operator to keep the tool aligned not with the outermost part of the port but with the natural rotation centre of the port, which is likely to be at some depth within the body.

According to the present invention there is provided a robot comprising: a base; a flexible arm extending from the base and having a plurality of joints whereby the configuration of the arm can be altered, a plurality of drivers arranged to drive the joints to move, a plurality of sensors for sensing the position of each of the joints and an attachment structure for attaching a tool to the arm, the joints permitting the angular attitude of the attachment structure relative to the base to be varied; and a control unit configured to control the drivers and to receive inputs from the sensors, and operable in a calibration mode in which, whilst a tool is attached to the attachment structure and captive in a port, it: (i) controls the drivers so as to permit the arm to be reconfigured by the action of an external force applied to the arm; (ii) monitors the configuration of the arm under the presence of an external force applied to the arm and transmitted through the tool to the port so as to cause the attitude of the attachment structure to the base to alter; whereby the location of the port can be estimated.

The control unit may be operable, subsequent to the said step (ii), to estimate the location of the port in dependence on the monitored configurations. The control unit may be configured to estimate the location of the port as a point through which a straight line extended with constant angular attitude relative to the attachment point is maintained under the presence of the external force. The control unit may be configured to store the estimated location.

The control unit may be operable in a driven mode in which, when a tool is attached to the attachment structure, it receives a demand signal indicating a desired location of a part of the tool, calculates a configuration of the arm in which the part of the tool will be at the desired location and the tool intersects the location of the port, and controls the drivers so the arm adopts the calculated configuration.

The control unit may be configured to, in the calibration mode, control the drivers so as to resist the action of gravity and thereby cause the arm to maintain a configuration imposed by the external force independently of the action of gravity.

The control unit may be configured to, in the calibration mode, control the drivers so as to present a limited resistance to reconfiguration under the external force independently of the action of gravity.

The control unit may be configured to, in the calibration mode, control the drivers so as to present increasing resistance to reconfiguration under the external force as the arm is moved so as to increase the deviation of the attitude of the attachment structure relative to the base from a neutral value.

The control unit may be configured to, in the calibration mode, control the drivers so as to resist angulation beyond a predetermined threshold of a tool attached to the arm.

The control unit may be configured to, in the calibration mode, control the drivers so as to resist translation beyond a predetermined threshold of a tool attached to the arm in a direction away from the interface between the tool and the arm.

The arm may comprise a plurality of position sensors for sensing forces applied about the joints. The control unit may be configured to, in the calibration mode, control the drivers in dependence on the outputs of the force sensors.

The control unit may comprise a processor and a memory storing non-transiently a set of instructions executable by the processor for implementing the calibration mode.

The robot may comprise a tool attached to the attachment structure, the tool being a surgical tool.

The robot may be a surgical robot.

According to a second aspect of the present invention there is provided a method for controlling a robot, the robot comprising a base; a flexible arm extending from the base and having a plurality of joints whereby the configuration of the arm can be altered, a plurality of drivers arranged to drive the joints to move, a plurality of sensors for sensing the position of each of the joints and an attachment structure for attaching a tool to the arm, the joints permitting the angular attitude of the attachment structure relative to the base to be varied; the method comprising, whilst a tool is attached to the attachment structure and captive in a port: controlling the drivers so as to permit the arm to be reconfigured by the action of an external force applied to the arm; monitoring the configuration of the arm under the presence of an external force applied to the arm and transmitted through the tool to the port so as to cause the attitude of the attachment structure to the base to alter; and thereby estimating the location of the port.

The external force can be applied other than by the drivers, e.g. by a user manually pushing on the arm.

The present invention will now be described by way of example with reference to the accompanying claims, in which:

A surgical robot may have an arm and a tool attached to the arm. The arm may have a series of flexible joints which allow the arm to be reconfigured and also allow the direction of the tool to be altered. The robot may be able to sense the configuration of its joints. For a surgical procedure a port can be sited in a patient. When it is necessary to calibrate the robot's knowledge of the port's location a tool on the arm can be inserted into the port. Then the arm can be moved generally transversely to the tool shaft, causing the port to apply a lateral force on the tool shaft. By monitoring the forces experienced by the arm as it is moved in that way and/or the configurations adopted by the arm in response to the lateral force imposed by the port, the location of the port, and particularly its natural rotation centre, can be estimated. That location can then be used, e.g. as a goniometric point for performing a subsequent procedure by means of the robot.

Figure 1:
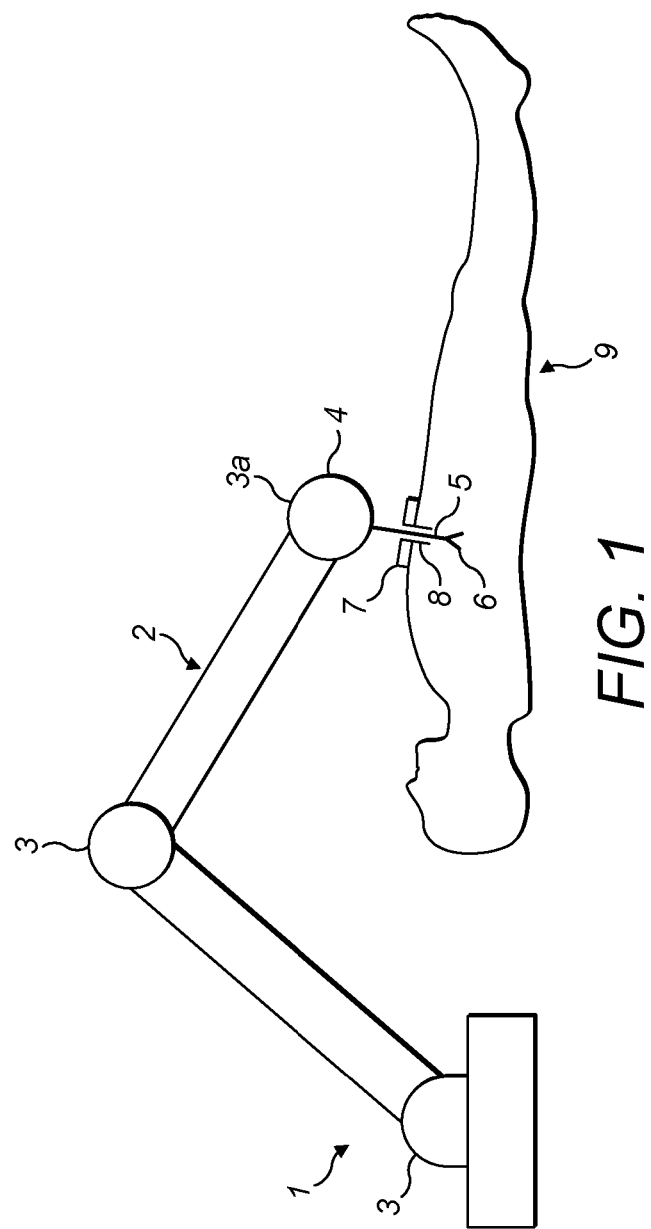
FIG. 1 shows a surgical robot performing a surgical procedure.
Figure 2:
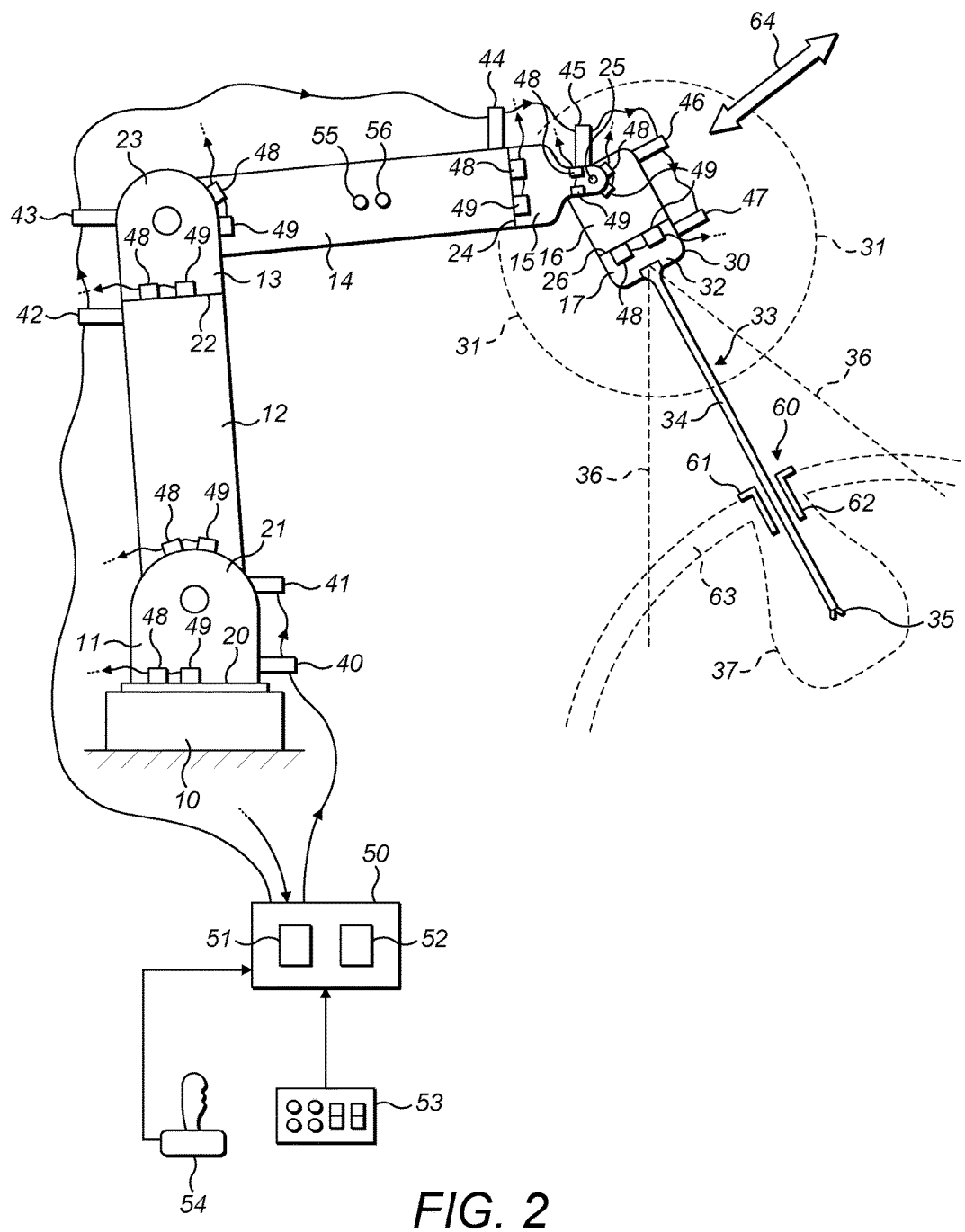
FIG. 2 shows a surgical robot.

FIG. 2 shows an example of a surgical robot. The robot comprises a base 10 which is fixed in place when a surgical procedure is being performed. The robot has a series of rigid arm members 11, 12, 13, 14, 15, 16, 17. The proximal arm member 11 is joined to the base 10 by a first revolute joint 20. Each other arm member in the series is joined to the preceding arm member by a respective joint 21, 22, 23, 24, 25, 26. Joints 21, 22, 23, 24 and 26 are revolute joints. Joint 25 is composed of two revolute joints whose axes are orthogonal to each other, as in a Hooke's or universal joint. The arm could be jointed differently from the arm of FIG. 2. For example, joint 23 could be omitted and/or joint 25 could permit rotation about a single axis. The arm could include joints that permit motion other than rotation between respective sides of the joint, for example a joint by which a tool attachment can slide linearly with respect to more proximal parts of the arm.

The joints are configured so that they provide the arm with flexibility allowing the distal end 30 of the robot arm to be moved to an arbitrary point in a three-dimensional working volume illustrated generally at 31. One way to achieve that is for the joints to have the arrangement illustrated in FIG. 2. There, the arm comprises the following joints:

- a most distal joint 20 having a substantially vertical rotation axis,
- a succeeding joint 21 having a rotation axis transverse to the axis of joint 20,
- a succeeding joint 22 having a rotation axis transverse to the axis of joint 21 and located between joint 21 and joint 23,
- a succeeding joint 23 having a rotation axis transverse to the axis of joint 22,
- a succeeding joint 24 having a rotation axis transverse to the axis of joint 23 and located between joint 23 and joint 25,
- a succeeding joint 25 having two mutually transverse rotation axes, one of which is transverse to the axis of joint 24, and
- a succeeding joint 26 having a rotation axis transverse to the other of the axes of joint 25.

Other combinations and configurations of joints could achieve a similar range of motion, at least within the zone 31. There could be more or fewer rigid arm members.

The distal end of the robot arm has an attachment 32 by means of which a surgical tool 33 can be releasably attached to the distal end of the arm. The surgical tool has a linear rigid shaft 34 and a working tip 35 at the distal end of the shaft. The working tip comprises a device for engaging in a medical procedure, for example a cutting, grasping or imaging device. There could be additional parts of the arm extending beyond the location where the tool is attached. The tool and/or the attachment 32 may be configured so that the tool extends linearly parallel with the rotation axis of the terminal joint 26 of the arm. In this example the tool extends along an axis coincident with the rotation axis of joint 26.

Joints 24, 25 of the robot are configured so that with the distal end of the arm held at an arbitrary location in the working volume 31 the surgical tool 33 can be directed in an arbitrary direction within a cone. Such a cone is illustrated generally at 36. One way to achieve that is for the terminal part of the arm to comprise the pair of joints 24, 25 whose axes are mutually arranged as described above. Other mechanisms can achieve a similar result. For example, joint 26 could influence the attitude of the tool if the tool extends out of parallel with the axis of joint 26.

The arm comprises a series of motors 40, 41, 42, 43, 44, 45, 46, 47. With the exception of the compound joint 25, which is served by two motors, each motor is arranged to drive rotation about a respective joint of the arm. The motors are controlled by a control unit 50. The control unit comprises a processor 51 and a memory 52. The memory stores, in a non-transient way, software code that can be executed by the processor to cause the processor to control the motors 40-47 in the manner described herein. The arm also comprises a series of sensors 48, 49. Conveniently these sensors comprise, for each joint, a position sensor 48 for sensing the positional state of the joint and a force sensor 49 for sensing applied torque about the joint's rotation axis. Compound joint 25 has two pairs of sensors. One or both of the position and torque sensors for a joint may be integrated with the motor for that joint. The outputs of the sensors are passed to the control unit where they form inputs for the processor 51. In addition, the processor receives inputs from a control panel 53, which allows the operating state of the arm to be selected, and from a three-dimensional controller 54, which allows an operator to signal to the control panel the three-dimensional movements required from the arm, e.g. when an operation is being performed.

The motion of the arm can be controlled in two modes. In a first, driven mode the configuration of the arm is set in dependence on the inputs received from the three-dimensional controller 54. In this mode the operator uses the three-dimensional controller to signal a desired position of the tool tip 35 and/or of the end 30 of the arm. The processor 51 determines a configuration of the joints of the arm that will result in the tool tip and/or the arm end being placed in that position. There may be multiple configurations of the arm that will result in the tool tip and/or the arm end being placed in the desired position. The processor may select between those configurations based on an algorithm that seeks to avoid collisions between the arm and other objects known to the processor to be near the arm, or that seeks to minimise the amount of movement of the joints to reach the new configuration. Once the processor has selected a new configuration it signals the joints 20-26 to adopt the states required to bring the arm into that configuration. In this way, in the driven mode the operator can signal the arm end and/or the tool tip to move to a desired location.

In a second, compliant mode the processor controls the arm to maintain a position in which it is placed by means of force applied directly to the arm. To achieve this the processor receives inputs from the position and force sensors 48, 49. From the position sensors the processor knows the current configuration of the arm. The memory 52 stores for each element of the arm, and the tool, its mass, the distance of its centre of mass from the preceding joint of the arm and the relationship between the centre of mass and the positional output of the joint sensor for the preceding joint. Using that information the processor models the effect of gravity on the elements of the arm for the current configuration of the arm and estimates a torque due to gravity on each joint of the arm. The processor then drives the motor of each joint to apply a torque that will exactly oppose the calculated gravitational torque. With this control strategy an operator can directly push or pull any part of the arm to a desired position, and the part will stay in that position notwithstanding the effect of gravity on it and on any parts depending from it. A force on the arm may result in a torque about multiple joints. The controller can be programmed to decide to prioritise certain ones of the joints for neutralising the torque. In the compliant mode the controller may automatically control the arm to maintain a configuration imposed by an external force independently of the action of gravity, to present a limited resistance to reconfiguration under the external force independently of the action of gravity and/or to control the drivers of the arm so as to present increasing resistance to reconfiguration under the external force as the arm is moved so as to increase the deviation of the attitude of the attachment structure relative to the base from a neutral value.

In the compliant mode some of the joints will experience no gravitational torque. The motors for those joints may be de-energised. More typically, each motor may be controlled in response to the torque measured about the respective joint. When the measured torque at a joint is adjusted for gravity any remaining torque represents a torque applied by a force due to a push on the arm or the tool. In response to that torque the controller may control the respective motor to move the joint in a direction so as to reduce the measured torque, and at a rate dependant on the magnitude of the measured torque, so that the arm provides the sensation of moving freely but with some resistance in response to applied force.

As discussed above, it is advantageous for the robot to be aware of the location of a surgical port through which it will be manipulating a tool. FIG. 2 shows a surgical port 60 inserted in the abdominal wall 63 of a patient. The port comprises an outer plate 61, which extends radially outwardly of an incision through the abdominal wall to resist the port being pushed too far into the abdominal cavity, and guide tube 62 which extends inwardly of the plate 61. A passageway extends through the port from the plate to the inner end of the tube. When the tool 33 is in place for performing a procedure on the patient the shaft 34 of the tool is inserted through the passageway into the abdominal cavity, as illustrated in FIG. 2.

Conveniently there is/are one or more joints near the terminal end of the arm that permit the tool to be rotated about one or more axes transverse to its main direction of elongation.

The present robot is capable of calculating the location of the port, and particularly the port's natural centre of rotation, by means of manipulation of the robot arm when the robot is in compliant mode. First, the patient is prepared for surgery by inserting the port into the appropriate location in the patient's body (e.g. the abdominal wall), and the patient is positioned in the operating theatre at a fixed location within reach of the robot. Then, with the robot in compliant mode an operator can grasp one or both of the robot arm and the tool 33 and push them into a configuration such that the elongate axis of the shaft 34 of the tool is aligned with the passageway in the port. Then the operator can push on the robot arm and/or the tool so that the tool moves parallel to its elongate axis and passes into the passageway in the port. At this stage the tool can conveniently be inserted only partially into the port, so that the tip 35 of the tool is still within the passageway 62 of the port.

Now, with the tool or instrument 33 located in the passageway 62 of the port the operator can move the distal end 30 of the robot arm in directions generally transverse to the tool shaft 34, e.g. as indicated generally at 64. This motion will cause the port to exert a lateral force on the tool shaft where it passes through the port, with the result that the tool will apply a torque to the joints of the arm—in this case joints 24 and 25—whose axes are transverse to the tool shaft axis. Since the robot is operating in compliant mode that torque will be accommodated by motion about the joints 24, 25. As the operator moves the distal end of the robot arm laterally the controller 50 receives inputs indicating the position of the joints. That information allows the controller to estimate: (a) the position of the distal end of the robot relative to the base and (b) the vector of the tool shaft relative to the distal end of the robot. Since the tool shaft passes through the passageway of the port, the passageway of the port must lie along that vector. As the distal end of the robot arm is moved, the controller can calculate multiple pairs of distal end positions and tool shaft vectors. Those vectors, will all converge, from their respective distal end position, on the location of the passageway of the port. By collecting a series of those data pairs and then solving for the mean location where the tool shaft vectors converge the robot controller can estimate the location of the port relative to the base.

To assist the controller 50 to estimate the port position the controller has knowledge of the relationship between the attitude of the terminal member 17 of the robot arm and the direction of the tool shaft 34. That relationship may be constant independent of the tool, by virtue of the interface 32 between the arm and the tool being standardised. Alternatively, different tools may extend from the terminal member at different angles, in which case the operator may inform the controller of the type of tool fitted to the robot arm, or the controller may automatically detect the type of tool and configure its port detection algorithm in dependence on information stored in memory 52 regarding the relationship between the tool and the attachment. Alternatively, the controller may detect the relationship between the attitude of the terminal member of the robot arm and the direction of the tool shaft through the motion of the joints (e.g. joints 24 and 25) as the terminal member of the robot arm is agitated by the operator during the calibration process. Conveniently the tool shaft is straight and extends in a known direction from the end member 32 of the robot arm.

In practice, the robot can be provided with a user input mounted near, and most conveniently on, the arm, such as push button 55. The controller is responsive to an operator pressing that button to enter a calibration mode in which it is compliant and repeatedly computes pairs of the position of the distal end of the robot and the direction of the tool shaft vector. It may perform those computations irregularly or at predetermined intervals, e.g. every 0.5 seconds. Once sufficient pairs of computations have been performed that the port location can be estimated with a satisfactory degree of precision, the controller estimates the port location. It then signals the user by means of a user output, such as light 56 or a sounder, which may again be on or near the arm, so that the user knows that the process of estimating the port location is complete. The controller then stores the location of the port in non-transient form in the memory 52 for later use.

The controller may cause the arm to enter or remain in the compliant mode automatically on the calibration mode being selected.

The number of data pairs that are needed to estimate the port's location with acceptable precision will depend on factors such as the accuracy of the arm's position sensors and the extent to which the operator moves the arm laterally during the calibration process. The controller may determine that the position has been estimated adequately once sufficient coherent measurements have been gathered that the variance between estimates of the position derived using successive measurements has reduced below a predefined level. Once more than two sets of arm joint data are available for configurations in which the tool passes through the goniometric point in the port there will be a calculable difference between the position estimates. The controller can gather data until this error estimate has reduced below a predetermined level. Conventional filtering and statistical methods can be used to make the error estimate.

It might assist in estimating the port location for the head 30 of the robot arm to be moved in two dimensions: e.g. with (i) components parallel to a direction that is transverse to the tool shaft (e.g. direction 64) and also with (ii) components orthogonal to that direction but transverse to the tool shaft. This can readily be done by having the operator gyrate the head 30, e.g. about a point generally aligned with the natural axis of the passage 62 in the port.

Thus, one manner of operation of the robot is as follows:
1. A port is placed in a patient, and the patient is located within working range of the robot, the robot and the patient being in their positions for a surgical procedure.
2. An operator places the robot in compliant mode, e.g. by using the control panel 53.
3. With the robot in compliant mode the operator locates the tool in the port.
4. The operator signals the controller to enter calibration mode by pressing button 55.
5. The operator gently agitates the head of the robot arm, causing the direction of the tool shaft to vary whilst the shaft continues to pass through the port.
6. The processor 51 of the robot controller 50 executes the code stored in memory 52 to estimate the location of the port as the location where the tool shaft vectors converge. Once the location of the port has been estimated with sufficient precision the controller stores the estimated location in a memory (e.g. memory 52), exits calibration mode and signals the user using light 56 so that the user knows to stop agitating the head of the robot arm.

Once the port location has been measured, knowledge of that location may be used to assist in controlling the configuration of the arm when the robot is operating in driven mode. When a procedure is being performed the controller 50 may permit an operator to direct the position of the tool tip 35 using the input device 54, and the controller may then automatically move the joints of the arm to a configuration where the tip will be at the desired position. The controller may be configured, by means of the software stored in memory 52, to select a configuration of the arm for which both (i) the tool tip is at the desired position and (ii) the shaft of the tool passes through the estimated port position, and to move the arm to that configuration. In that way the tool tip can be provided at the desired position but with relatively little disruption to the outer tissues of the patient.

The location of the port may also be used to assist insertion of a tool into the patient. Once a tool has been attached to the arm, and is to be inserted through the port the controller may automatically control the arm to adopt a configuration in which the tool is generally aligned with the port passage (e.g. based on the initial location from which the configuration mode was initiated) and the tool tip is located close to but outside the port. Then an operator can insert the tool through the port either by physically manipulating the robot arm with the arm in compliant mode or by controlling the arm in driven mode using the input device 54.

The location of the port may also be used to help avoid damage to the patient through erroneous motion of the tool tip. A working zone 37 within the patient may be defined with reference to the location of the port. Then the controller may resist or prevent motion of the tool tip outside the working zone. The working zone may be defined by an operator before undertaking an invasive procedure. The controller may resist motion of the tool tip outside the working zone by requiring the operator to make an additional input to override the working zone protection before the controller will permit the tool tip to go outside the predefined working zone, or by presenting an alert to the operator if the tool tip goes outside the working zone.

When the calibration procedure is being performed, the angulation of the tool varies, and hence the port 62 will be rotated somewhat with respect to the patient. A consequence of this is that the calibration procedure estimates the location of the natural rotation centre of the port rather than the location of the exterior of the port as in prior methods. The natural rotation centre of the port will depend on the compliance of the outer tissues of the patient, through which the port passes. Because of this, if during a subsequent procedure the controller maintains the tool shaft passing through that natural rotation centre damage to the patient's outer tissues can be reduced in comparison with other methods.

If the distal end of the robot arm is moved excessively in a lateral sense during the calibration procedure then that could result in excessive angulation of the port and hence unnecessary damage to the patient. This can be limited through training the operator to gyrate the distal end of the robot arm by an appropriate amount. However, the controller 50 may also restrict the motion of the head during the calibration process. At the start of the calibration process the distal end of the robot arm can be assumed to be in a neutral position generally aligned with the axis of the port. During the calibration process the controller knows the distance by which the distal end of the robot has moved transversely to the tool shaft since calibration was initiated. If that distance exceeds a predetermined threshold then the controller can control the motors of the arm to reduce the arm's compliance by resisting further motion of the distal end of the robot arm away from the neutral position. The controller's estimate of the neutral position for this purpose can be refined as it develops measurement pairs and builds up at least a rough estimate of the position of the port.

If the distal end of the robot arm is moved excessively in a longitudinal sense further into the patient during the calibration procedure then that could result in excessive travel of the tool into the body of the patient, potentially causing injury to the patient. This can be limited through training the operator to gyrate the distal end of the robot arm in a predominantly lateral sense. However, the controller 50 may also restrict the longitudinal motion of the head during the calibration process. At the start of the calibration process the tool can be assumed to be aligned with the port and inserted into the port by an acceptable amount. During the calibration process the controller knows the distance by which the distal end of the robot has moved parallel with to the tool shaft and away from the proximal end of the tool since calibration was initiated. If that distance exceeds a predetermined threshold then the controller can control the motors of the arm to reduce the arm's compliance by resisting further motion of the distal end of the robot arm away from the neutral position. That predetermined threshold may be zero.

The principles described above are applicable to other types of surgical robot than the one shown in FIG. 2. For example, the base of the robot could be floor-mounted, ceiling-mounted or mounted to a bed, trolley or table. The joints and members of the robot arm could be provided in any suitable way. The terminal element of the robot could be provided with a sliding rail by means of which the tool can be inserted through the port. The robot could be for purposes other than surgery. For example, the port could be an inspection port in a manufactured article such as a car engine and the robot could control a viewing tool for viewing inside the engine.

The device provided on the tool tip could be for any appropriate surgical or other procedure, for example cutting, holding, viewing, illuminating, irradiating or joining. The tool could be a tool having a non-functional tip and intended simply for calibration procedures. In the examples given above the shaft of the tool is straight, as is the passage in the port. This characteristic assists in inserting the tool through the port and makes the calculation of the port location easier, but the tool shaft and the port passage could be curved with a common radius.

The three-dimensional controller 54 could be remote from the robot. The controller 50 could operate the robot arm under programmatic control.

The position sensors could, for example, be potentiometers, optical position encoders, ultrasonic or radio distance sensors. The force sensors could, for example, be a resistance-based strain gauge, a piezoelectric strain gauge or a semiconductor strain gauge. The drivers for driving the joints of the robot to move could be rotary or linear motors, or means other than motors: for example hydraulic or pneumatic rams.

When the position of the port is being detected the motors could be inactive, so they do not even oppose gravity. If the arm were entirely flexible then the force sensors could be omitted. However, this would make it more difficult for the operator to manipulate the arm without the tool imposing excessive load on the patient.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robot comprising:
 a base;
 a flexible arm extending from the base and having a plurality of joints whereby the configuration of the aim can be altered, a plurality of drivers arranged to drive the joints to move, a plurality of sensors configured to sense the position of each of the joints and an attachment structure configured to attach a tool to the arm, the joints permitting the angular attitude of the attachment structure relative to the base to be varied; and
 a control unit configured to control the drivers and to receive inputs from the sensors indicating the position of the joints, and operable in a calibration mode in which, whilst a tool is attached to the attachment structure and captive in a port, it:
 (i) controls the drivers so as to permit the aim to be reconfigured by the action of an external force applied to the arm;
 (ii) from the sensor inputs indicating the position of the joints, monitors the configuration of the arm under the presence of each of a plurality of external forces applied to the arm and transmitted through the tool to the port so as to cause the attitude of the attachment structure to the base to alter; and
 (iii) estimates the natural centre of rotation of the port from the monitored arm configurations.

2. A robot as claimed in claim 1, wherein the control unit is configured to estimate the natural centre of rotation of the port as a point through which a straight line extended with constant angular attitude relative to the attachment point is maintained under the presence of each external force.

3. A robot as claimed in claim 2 wherein the control unit is configured to store the estimated natural centre of rotation of the port.

4. A robot as claimed in claim 3, the control unit being operable in a driven mode in which, when a tool is attached to the attachment structure, it receives a demand signal indicating a desired location of a part of the tool, calculates a configuration of the arm in which the part of the tool will be at the desired location and the tool intersects the natural centre of rotation of the port, and controls the drivers so the aim adopts the calculated configuration.

5. A robot as claimed in claim 1, wherein the control unit is configured to, in the calibration mode, control the drivers so as to resist the action of gravity and thereby cause the arm to maintain a configuration imposed by each external force independently of the action of gravity.

6. A robot as claimed in claim 1, wherein the control unit is configured to, in the calibration mode, control the drivers so as to present a limited resistance to reconfiguration under each external force independently of the action of gravity.

7. A robot as claimed in claim 1, wherein the control unit is configured to, in the calibration mode, control the drivers so as to present increasing resistance to reconfiguration under each external force as the arm is moved so as to increase the deviation of the attitude of the attachment structure relative to the base from a neutral value.

8. A robot as claimed in claim 1, wherein the control unit is configured to, in the calibration mode, control the drivers so as to resist angulation beyond a predetermined threshold of a tool attached to the arm.

9. A robot as claimed in claim 1, wherein the control unit is configured to, in the calibration mode, control the drivers so as to resist translation beyond a predetermined threshold of a tool attached to the arm in a direction away from the interface between the tool and the arm.

10. A robot as claimed in claim 1, wherein the arm comprises a plurality of force sensors configured to sense forces applied about the joints, and the control unit is configured to, in the calibration mode, control the drivers in dependence on the outputs of the force sensors.

11. A robot as claimed in claim 1, wherein the control unit comprises a processor and a memory configured to store non-transiently a set of instructions executable by the processor for implementing the calibration mode.

12. A robot as claimed in claim 1, comprising a tool attached to the attachment structure, the tool being a surgical tool.

13. A robot as claimed in claim 1, wherein the robot is a surgical robot.

14. A method configured to control a robot, the robot comprising a base; a flexible arm extending from the base and having a plurality of joints whereby the configuration of the arm can be altered, a plurality of drivers arranged to drive the joints to move, a plurality of sensors configured to sense the position of each of the joints and an attachment structure configured to attach a tool to the arm, the joints permitting the angular attitude of the attachment structure relative to the base to be varied; the method comprising, whilst a tool is attached to the attachment structure and captive in a port:

control the drivers so as to permit the arm to be reconfigured by the action of an external force applied to the aim;

from the sensor inputs indicating the position of the joints, monitoring the configuration of the aim under the presence of each of a plurality of external forces applied to the arm and transmitted through the tool to the port so as to cause the attitude of the attachment structure to the base to alter; and estimating the natural centre of rotation of the port from the monitored arm configurations.

* * * * *